(12) United States Patent
Jaspers et al.

(10) Patent No.: US 8,101,216 B2
(45) Date of Patent: Jan. 24, 2012

(54) SELF-ADHESIVE SKIN PATCH AND COMBINATION SET FOR COSMETIC SKIN CARE

(75) Inventors: Soeren Jaspers, Schenefeld (DE); Carsten Hartkopf, Hamburg (DE); Christian Gaede, Neu Wulmstorf (DE); Stefan Bodenschatz, Buxtehude (DE); Katharina Post, Den Haag (NL); Jens Schulz, Schenefeld (DE); Karl-Heinz Woeller, Hamburg (DE)

(73) Assignee: Beiersdorf AG, Hamburg (DE)

( * ) Notice: Subject to any disclaimer, the term of this patent is extended or adjusted under 35 U.S.C. 154(b) by 723 days.

(21) Appl. No.: 11/547,098

(22) PCT Filed: Mar. 29, 2006

(86) PCT No.: PCT/EP2006/061137
§ 371 (c)(1),
(2), (4) Date: Jan. 10, 2007

(87) PCT Pub. No.: WO2006/120066
PCT Pub. Date: Nov. 16, 2006

(65) Prior Publication Data
US 2008/0038300 A1 Feb. 14, 2008

(30) Foreign Application Priority Data

May 13, 2005 (DE) .......................... 10 2005 023 149
Nov. 11, 2005 (DE) .......................... 10 2005 053 909

(51) Int. Cl.
*A61K 36/82* (2006.01)
(52) U.S. Cl. .......................... 424/729; 424/401; 424/448
(58) Field of Classification Search .......................... None
See application file for complete search history.

(56) References Cited

U.S. PATENT DOCUMENTS

| 3,770,780 A | 11/1973 | Hirsch |
| 3,790,533 A | 2/1974 | Samour |
| 3,900,610 A | 8/1975 | McKenna, Jr. |
| 4,795,638 A | 1/1989 | Ayache et al. |
| 4,978,531 A | 12/1990 | Yamazaki et al. |
| 5,126,144 A | 6/1992 | Jaeger et al. |
| 5,162,410 A | 11/1992 | Sweet |
| 5,196,259 A | 3/1993 | Pierini et al. |
| 5,215,759 A | 6/1993 | Mausner |
| 5,273,757 A | 12/1993 | Jaeger et al. |
| 5,306,502 A | 4/1994 | Jaeger et al. |
| 5,411,739 A | 5/1995 | Jaeger et al. |
| 5,482,988 A | 1/1996 | Ulman et al. |
| 5,523,090 A | 6/1996 | Znaiden et al. |
| 5,572,536 A | 11/1996 | Thiruvengadam |
| 5,603,948 A | 2/1997 | Merkle et al. |
| 5,607,721 A | 3/1997 | Ulman et al. |
| 5,658,975 A | 8/1997 | Ulman et al. |
| 5,730,999 A | 3/1998 | Lehmann et al. |
| 6,346,255 B1 | 2/2002 | Fotinos |
| 6,419,935 B1 | 7/2002 | Gueret |
| 6,589,194 B1* | 7/2003 | Calderon et al. .............. 601/151 |
| 6,698,162 B2* | 3/2004 | Shudo et al. ..................... 53/428 |
| 6,878,367 B2 | 4/2005 | Picard-Lesboueyries |
| 7,037,514 B1 | 5/2006 | Horizumi et al. |
| 2001/0007671 A1 | 7/2001 | Gueret |
| 2002/0054928 A1 | 5/2002 | Picard-Lesboueyries |
| 2002/0160064 A1 | 10/2002 | Zulli et al. |
| 2002/0192273 A1* | 12/2002 | Buseman et al. ............. 424/449 |
| 2003/0082217 A1 | 5/2003 | Afriat et al. |
| 2003/0152612 A1 | 8/2003 | Pugliese et al. |
| 2004/0009202 A1 | 1/2004 | Woller |
| 2004/0116356 A1 | 6/2004 | Malik |
| 2004/0143026 A1 | 7/2004 | Shah |
| 2004/0157800 A1 | 8/2004 | Buononato et al. |
| 2004/0161435 A1 | 8/2004 | Gupta |
| 2004/0175351 A1* | 9/2004 | Liu et al. ......................... 424/74 |
| 2004/0228884 A1 | 11/2004 | Gupta |
| 2005/0281869 A1* | 12/2005 | Kruse et al. ................... 424/449 |
| 2005/0281881 A1 | 12/2005 | Woeller et al. |
| 2006/0134147 A1 | 6/2006 | Kalafsky |
| 2006/0182787 A1* | 8/2006 | Jaenichen et al. ............ 424/445 |
| 2006/0252706 A1 | 11/2006 | Kim et al. |

FOREIGN PATENT DOCUMENTS

| CA | 2367394 | 9/2000 |
| DE | 4222334 | 1/1994 |
| DE | 4224325 | 2/1994 |
| DE | 4310012 | 9/1994 |
| DE | 19911262 | 9/2000 |
| DE | 10056010 | 5/2002 |
| DE | 10260873 | 7/2004 |
| EP | 0303445 | 2/1989 |
| EP | 0305757 | 3/1989 |
| EP | 0452034 | 10/1991 |
| EP | 0493151 | 7/1992 |
| EP | 0507160 | 10/1992 |
| EP | 0663431 | 7/1995 |
| EP | 0728472 | 8/1996 |
| EP | 0970707 | 1/2000 |
| EP | 0976382 | 2/2000 |

(Continued)

OTHER PUBLICATIONS

Registry entry for methyl 4-hydroxybenzoate—accessed Jun. 2008.*
English Language Abstract of EP 1 161 937.
English Language Abstract of DE 198 25 693.
English Language Abstract of JP 11-228340.
English Language Abstract of JP 4-178323.
English Language Abstract of DE 42 22 334.
Auchter et al., "Acrylic Adhesives", chapter 19 in "Handbook of Pressure Sensitive Adhesive Technology", Third Edition, edited by Donatas Satas, Satas & Associates, Warwick, RI, 1999, pp. 444-514.

*Primary Examiner* — Susan Hoffman
(74) *Attorney, Agent, or Firm* — Greenblum & Bernstein, P.L.C.

(57) ABSTRACT

The present invention relates to a skin patch comprising a matrix adhering to the skin and containing at least one active cosmetic substance and a combination with a skin wrapping to generate an effective compression for the treatment of cellulite and/or striae.

39 Claims, 1 Drawing Sheet

FOREIGN PATENT DOCUMENTS

Figure 1:
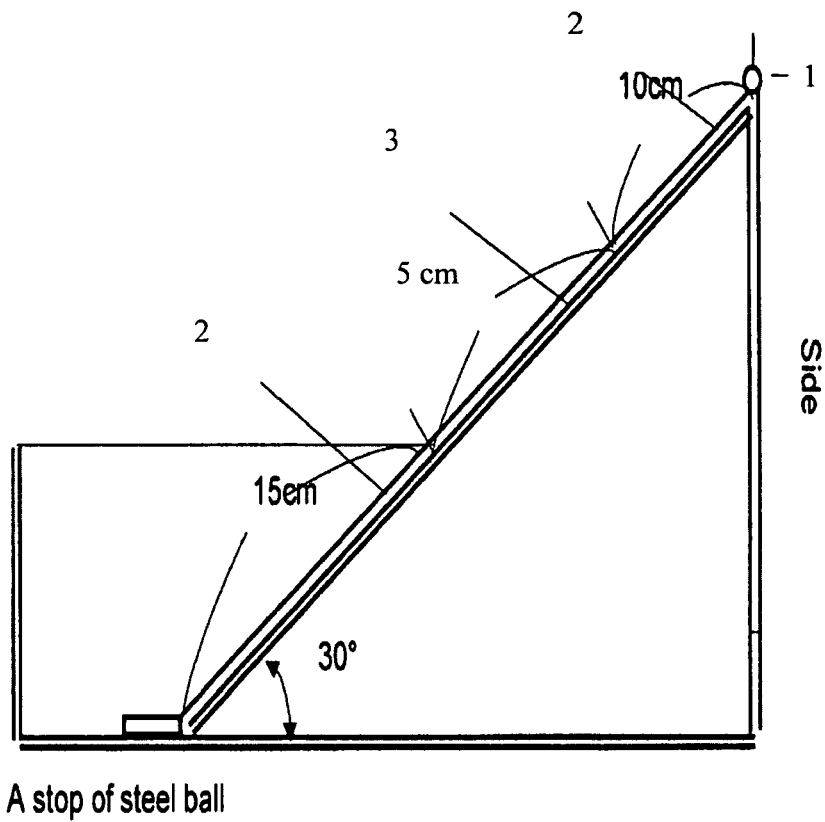
Figure 1:
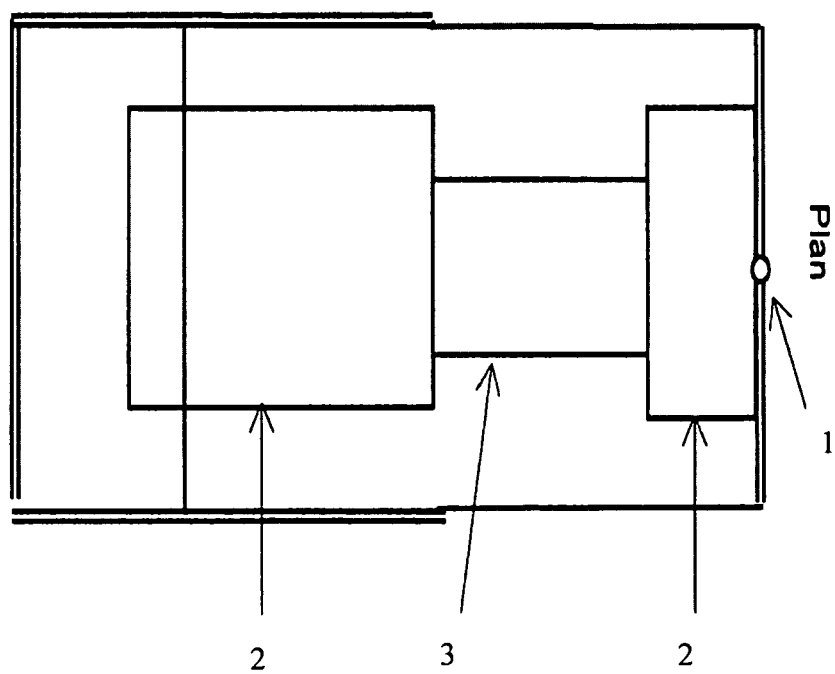

| | | |
|---|---|---|
| EP | 1136057 | 9/2001 |
| EP | 1161937 | 12/2001 |
| EP | 1181926 | 2/2002 |
| EP | 1234572 | 8/2002 |
| GB | 2166954 | 5/1986 |
| JP | 4/178323 | 6/1992 |
| JP | 11-228340 | 8/1999 |
| WO | 94/02123 | 2/1994 |
| WO | 19825693 | 12/1999 |
| WO | 2004/058315 | 7/2004 |
| WO | 2004/060268 | 7/2004 |
| WO | 2004/074216 | 9/2004 |
| WO | 2004/093865 | 11/2004 |
| WO | 2005/007127 | 1/2005 |
| WO | 2006/068715 | 6/2006 |

* cited by examiner

A stop of steel ball

SELF-ADHESIVE SKIN PATCH AND COMBINATION SET FOR COSMETIC SKIN CARE

CROSS-REFERENCE TO RELATED APPLICATIONS

The present application is a U.S. National Stage of International Application No. PCT/EP2006/061137, filed Mar. 29, 2006, which claims the priorities of German Patent Application No. 10 2005 023149.7, filed May 13, 2005 and German Patent Application No. 10 2005 053909.2, filed Nov. 11, 2005.

BACKGROUND OF THE INVENTION

1. Field of the Invention

The present invention relates to a skin patch comprising a matrix which adheres to the skin and contains at least one active cosmetic substance and a combination with a skin wrap to produce an effective compression for treating cellulite and/or stretch marks of the skin, such as, e.g., striae.

2. Discussion of Background Information

Cellulite (medical term: dermopanniculosis) is not a disease, but a cosmetic problem.

The reasons for cellulite lie above all in the special structure of female skin and in the reaction to female hormones. Fat cells are stored in the hypodermis. Their quantity is already determined in infancy and cannot be influenced by diet or sport. The fatty acids from diet are converted into fats in the fat cells and are stored in the connective tissue in a nodular manner. If these fats are not broken down for a long period (e.g., sport) and if the body in addition is overfed, the cells can expand by a multiple of their size. The enlarged cells then push through the connective tissue and the feared orange peel skin occurs, also known as cellulite.

The further consequences in old age are small varicose dilatations of the cutaneous veins, varicose veins, thrombosis and leg complaints. The thighs often also store superfluous fat that is absorbed through the diet. The unsightly thickening at the sides of the thighs, also known as saddle bags, combined with cellulite, is often a great strain on those affected.

The so-called body wrap principle is known for treating cellulite. A special body wrap gel is applied to the problem areas thereby and they are subsequently wrapped in a wrapping foil. A heat effect is thereby produced and a purification of the tissue takes place through the active substances of the body wrap gel and the heat development.

Through the application of the gel and the wrap shorts, the lymphatic circulation is to be stimulated and through the heat generation toxins, fats and wastes are to be removed from the body. in this manner Striae are also reduced, cellulite is reduced and the so-called saddle bags are also reduced after only a few treatments.

Anti-cellulite plasters (e.g., "Perfect Slim Cellulite Patch" from L'Oréal) are also known, the components of which, such as seaweed or caffeine, promote the smoothing of the unsightly dimples. The beauty plasters in particular make the application easier for women who are tired of having to apply cream all the time. Thus areas particularly affected can be treated in a targeted manner. The advantage of a patch of this type lies in the continuous dispensing of active substances over eight hours by the plaster. Moreover, these can also be used at night.

The preparation CREALITE by Creaderm uses nanotechnology against cellulite for the first time. Caffeine is transported through the skin into the subcutaneous fatty tissue with liposomes.

CREALITE contains large-dose caffeine (2%) in a specially suitable carrier. Caffeine withdraws water from the cells and in addition inhibits the enzyme cyclic M3',5'-nucleotide phosphodiesterase, through which a weight loss is to be achieved. The fat cells which are very much enlarged with cellulite are to be made smaller thereby and the skin is to appear tauter and smoother again.

WO 05/007127, WO 04/093865, WO 04/074216 and WO 04/060268 likewise highlight numerous cosmetic active substances and treatment methods for cellulite.

EP 1181926, EP 728472 and EP 493151 likewise disclose in particular cosmetics containing caffeine for cellulite treatment.

The object of the present invention is to disclose alternatives for the treatment of cellulite.

Stretch marks in the skin after pregnancy which impair the on the aesthetic appearance are an annoying cosmetic phenomenon. So-called stretch marks are also called striae. This is not a disease, but a purely cosmetic problem.

Skin stretch marks (striae) are tears in the subcutaneous tissue. They occur on the abdomen, hips or breast. Striae are bluish red at first, then yellowish white. They have a similar appearance to scars. They occur whenever the skin is overstretched and at the same time the elasticity of the skin has decreased. A high cortisone level promotes the formation of stretch marks. This hormone allows the skin to retain more water and it reduces the elasticity of the skin.

If the skin is stretched by a pregnancy or weight gain, small tears occur in the elastic tissue. The skin becomes thinner at the affected areas and the blood vessels shine through in a bluish color. Later the areas form a scar and the marks become white. Unfortunately, they will not disappear again.

Pregnant women, people in puberty, competitive athletes, people undergoing hormone treatment and people with increased weight are the groups most affected by Striae.

During pregnancy there is a higher cortisone level in the blood. Stretch marks occur here in the skin of the abdomen in the case of many women. They are called "striae gravidarum" or pregnancy stretch marks.

Once stretch marks are present, according to the current standard of knowledge they cannot be completely reduced. A reduction and abatement up to 50% is possible. It also applies to laser treatments that they do not usually achieve the desired success.

The object of the present invention is therefore also to provide a skin patch that renders possible a treatment of the skin areas affected by striae and brings about a cosmetic improvement of these skin areas.

The skin is exposed to constantly changing environmental influences and over time is subject to a number of changes. Thus changes in the barrier properties, the degree of skin wrinkles and elasticity, pigmentation and in particular, due to exogenic influences, also inflammatory reactions and, e.g., also after-reactions of the skin to the impact of UV radiation result.

The barrier effect of the skin can be quantified via the determination of the transepidermal water loss (TEWL). This is the evaporation of water from the interior of the body without including the loss of water during sweating. The determination of the TEWL value has proven to be extraordinarily informative and can be used for the diagnosis of cracked or chapped skin, to determine the tolerance of surfactants with different chemical structures and the like.

The proportion of water in the top dermal layer is very important for the beauty and well-groomed appearance of the skin. It can be favorably influenced to a limited extent by introducing moisture regulators.

Cosmetic skin care means primarily strengthening or rebuilding the natural function of the skin as a barrier against environmental influences, e.g., dirt, chemicals, microorganisms, and against the loss of endogenous substances, e.g., water, natural fats, electrolytes.

If this function is impaired, an intensified absorption of toxic or allergenic substances or an attack by microorganisms leading to toxic or allergic skin reactions can occur.

The aim of skin care is furthermore to compensate for the loss by the skin of lipids and water caused by daily washing. This is particularly important if the natural regenerative ability is insufficient. Moreover, skin care products should protect against environmental influences, in particular sun and wind, and delay skin aging.

Chronological skin aging is caused, e.g., by endogenous, genetically determined factors. The following structural damage and functional disorders, which can also come under the term "senile xerosis", can occur, e.g., in the epidermis and the dermis due to aging:
(a) dryness, roughness and the formation of small lines due to dryness,
(b) itching and
(c) reduced regreasing by sebaceous glands (e.g., after washing).

Exogenous factors, such as UV light and chemical noxae, can have a cumulative effect. In the epidermis and dermis, in particular due to exogenic factors, e.g., the following structural damage and functional disorders occur in the skin:
(d) increased susceptibility to mechanical stress (e.g., cracking).

Products for the care of sensitive, itchy or dry skin or products for the treatment or prophylaxis of DNS damage are known per se. However, their effectiveness is limited.

It is therefore the object of the present invention to provide in particular cosmetic skin patches that offer an additional effective protection from harmful oxidation processes in the skin as well as offering additional protection from or helping to reduce dryness, roughness and the formation of wrinkles due to dryness, itching, reduced regreasing by sebaceous glands, e.g., after washing, and increased susceptibility to mechanical stress, e.g., cracking.

Preparations are known in the prior art which, applied to the skin or the mucous membranes, are to have a moisturizing and cooling effect. In the literature for example ionic compounds, in particular ammonium salts, are described as cooling agents. Isopropanol gels with added camphor and menthol are also widely used as cooling preparations, and essential oils, primarily camphor and menthol, but also derivatives thereof, e.g., menthyl lactate or menthyl-3-hydroxybutyrate, are generally frequently incorporated into cooling compositions.

Menthol, camphor and derivatives thereof, as well as other essential oils, lower the stimulus threshold of neuronal cold receptors and thus produce a cold sensation. However, they often cause an increase in blood supply at the same time, which in contrast generates a sensation of heat. The application of these substances, especially on irritated skin, is at any rate problematic. Moreover, many of these compounds have poor water solubility. Their use is consequently limited to a few cosmetics and dermatics.

The object of the present invention is therefore also to provide a skin patch that does not have the listed disadvantages or has a reduced level thereof while moisturizing, cooling and/or increasing blood supply.

In the case of plaster systems that contain active substances and remain on the skin for a long time, a main focus is naturally on the skin tolerance of the adhesive matrix. It is expected to be not irritating to the skin, to have good adhesion, in particular over a longer application period, and to guarantee a painless removal of the plaster or pad without leaving a residue. This expectation is not met by many known adhesive substances, such as rubber, silicone, resins or styrene hydrocarbons, which are used in particular to improve the adhesive properties. These known adhesive substances often lead to the occurence of skin irritations, allergies, macerations and/or a painful removal of the plaster from the skin.

The therapeutic mechanism of plasters or cosmetic matrices for administering cosmetic substances into and onto the skin are subject to an analogous functional principle such as Transdermal Therapeutic Systems (TTS). The terms plaster, cosmetic/dermatological matrices and cosmetic/dermatological pads are used synonymously below.

Transdermal Therapeutic Systems for dispensing active substances into or through the skin have been known for a long time and represent plaster-type systems, in particular delivering medicinal agents The topical application of cosmetic and dermatological active substances via plaster systems or cosmetic matrices offers two main advantages:
firstly, this form of administration produces first-order release kinetics of the active substance, thereby allowing a constant level of the active substance to be maintained in the skin over a long period of time.
secondly, an additional intensive care of the skin can be effected via suitable systems.

The time-dependent release of the cosmetic active substance from a TTS occurs depending on its TTS/skin distribution coefficient and its diffusion in the region of the TTS and the skin.

Both factors are determined by the composition of the matrix, thereby allowing the amount released per time unit and the duration of effectiveness to be directly influenced. Usually hydrocolloids, solubilizers and enhancers are used, allowing an improved solubility and diffusion as well as a faster transfer of the substance from TTS into the skin.

Ideally, first-order release kinetics are achieved, allowing the release of equal quantities per time unit.

One embodiment of transdermal systems of this type which has been well described in the technical literature is that of matrix systems or monolithic systems in which the active cosmetic agent is incorporated directly into the pressure-sensitive adhesive. In the ready-to-apply product a pressure-sensitive adhesive matrix of this kind, comprising the active substance, is equipped on one side with a backing, which is impermeable for the active substance, while on the opposite side there is a backing film equipped with a release layer, which is removed prior to application to the skin (kleben&dichten, No. 42, 1992, pp. 26 to 30).

The aforementioned properties of a TTS avoid the need for frequently repeated application and avoid burdening the skin with high concentrations of active substances, and so reduce irritation to the skin, which is unavoidable in the event of repeated administration of liquid and semisolid administration forms.

In summary, the advantages of the TTS lie in a distinctly improved compliance on the part of users, which is attributable to the simple and rapid administration and to the long-lasting efficacy of transdermal therapeutic systems.

One basic requirement of a TTS is effective adhesion to skin, which must be maintained over the entire period of the intended dosing of the active substance, and another is the ability for the TTS to be removed without leaving any residue. Painful redetachment of the active substance patch after a prolonged period of wear is a frequent observation. Apart from adhesives which are coated in solution onto the backing, the adhesives used also include solvent-free systems, such as hot-melt adhesives. A feature of these adhesives is that in the course of their coating it is possible to forego the use of organic solvent and dispersion media. Hot-melt adhesives are converted to a liquid form by heating and are applied thus as a melt to the respective patch backing. Apart from technical aspects, such as solvent processing, plant design with anti-explosion measures, and environmental protection strictures, medical reasons also play a part in the choice of solvent-free adhesives. Transdermal therapeutic systems are generally applied to healthy, intact skin.

Self-adhesive matrix systems for administering active cosmetic substances are among traditional applications in Asia, particularly in Japan, and are defined in the Japanese pharmacopoeia under the term "cataplasm." Cataplasms, accordingly, are commonly prepared by mixing glycerin, water or other suitable liquids with finely pulverized active substances, with the addition of essential oils.

Glycerin functions here as a humectant, in order to prevent the cataplasms from drying out prematurely in use.

Whereas in the traditional Asian preparations natural thickeners such as alumina, etc., are employed, recent decades have seen the use, more and more, of modern synthetic raw materials, such as polyacrylic acid as a gel former, for example, for their production. This allows the cataplasms, which are commonly pasty, to be produced as hydrogel matrices having improved attractiveness and user-friendliness. EP 1 136 057 describes an aqueous gel system for cosmetic use without backing or liner, with a light transmittance of min. 70%.

EP 0 507 160 describes cataplasms containing lidocaine.

A disadvantage of the cataplasms described is that the production of the base matrices requires many different individual components such as gel formers, thickeners, plasticizers, humectants, stabilizers, emulsifiers, pH regulators, antioxidants, etc., and possibly also solubilizers and penetration enhancers in the case of active substance cataplasms. Since the adhesive performance and consistency of such a matrix is a function of the interaction of all of the individual components, targeted product development/optimization with regard to these fundamental product requirements is, correspondingly, time-consuming and difficult.

The production of polymer matrices, especially gel matrices, from polyacrylates has likewise been known for many years and is described for example in EP 0 507 160, JP 11-228340 and JP 04178323. Gel matrices are used, among other things, as an adhesive base and as an active substance reservoir in transdermal systems. Such systems have an adequate bond strength, especially to moist skin (buccal patches), but because of inadequate cohesiveness cannot be removed again completely when required.

In order to form a gel with a defined structure it is necessary for polyacrylic acid to be cross-linked. The nature of the cross-linker makes a critical contribution to the structure of the resultant gel. The customary cross-linking agents may be metal ions (e.g.: $Al^{3+}$ ions), or organic compounds. Cross-linking with aluminum salts proceeds via the coordination of the oxygen functions of the polyacrylic acid to the $Al^{3+}$ ions. A very close-meshed gel with high viscosity is formed, the viscosity of the gel being controllable only via the amount of cross-linker (Handbook of Pressure Sensitive Adhesive Technology, page 458 if, 1999).

JP 11-228340 discloses polyacrylic acid-based gels which utilize $Al^{3+}$ compounds as cross-linkers. The use of the mandatory aluminum compound as a cross-linking agent is limited, since otherwise the physical properties of the gel are impaired. If the proportion of aluminum cross-linker is too high the gel becomes too hard.

Further examples of cross-linking with polyvalent metal ions are known from the literature, e.g., U.S. Pat. No. 3,900,610 (zinc salts), U.S. Pat. Nos. 3,770,780 or 3,790,533 (titanium compounds). Ionic cross-linking with metal ions leads to hard, viscous polymer gels with low tack (Handbook of Pressure Sensitive Adhesive Technology, page 458 ff, 1999).

EP 303445 discloses a patch with a monolithic gel matrix based on water-soluble polymers. Mandatory constituents are clebopride or a pharmaceutically acceptable salt thereof as active substance, water, water absorbers, and water-soluble polymers. As water-soluble polymers one skilled in the art is able to select from a range of known polymers such as polyvinyl alcohol, gelatin, polyacrylic acid, sodium polyacrylates, methylcellulose, carboxymethylcellulose, polyvinylpyrrolidone, rubber and other cross-linkable polymers and also mixtures thereof.

EP 976382 describes a patch comprising a matrix composed of a system which is hydrophilically gelling in aqueous phase and which is formed from gelan gum and at least one further hydrocolloid. Gelan gum is claimed mandatorily. Gelan gum is understood by one skilled in the art, as defined by technical dictionaries, to comprise hydrocolloids obtained from the following marine plants: Agardhiella tenera, Furcellaria fastigiata, Hypnea cervicornis, musciformis, spicifera, Suhria vitata. Nor is there any mention of the essential aspects of self-adhesive properties, the adjustability of bond strength and elasticity of the resultant matrices.

A further problem associated with the cross-linking of polyacrylic acid to form a self-adhesive matrix or gel is that a matrix once produced, having defined physical properties, viscosity, tack, etc., must have the same defined properties in a later production process. This reproducibility is difficult if not impossible to realize with the cross-linking technologies that are currently known.

It is also known that the adhesive composition of the plaster can be employed as the matrix comprising the active substance. In addition to self-adhesive compositions applied from solution, hot-melt self-adhesive compositions have also been proposed for this purpose, as for example in EP 0 663 431 A, EP 0 452, 034 A, EP 0 305 757 A, DE-A 43 10 012, DE-A 42 22 334 and DE-C 42 24 325. The active substances listed in these documents, if named at all, are systemic ones.

As examples of active substance plasters, mention may be made of the active substance plasters which aid the circulation, belonging to the group of locally active therapeutic systems. The use of such plasters is indicated for the treatment of rheumatic complaints, sciatica, lumbago, stiff neck, shoulder/arm pain and muscular strains and sprains, muscular aching, or muscle, joint and nerve pain in the region of the locomotor system.

Capsaicin and nonivamide are known active substances in such locally acting plasters that aid the circulation. Because of their use on the locomotor system they are in general required to adhere strongly. Usually, the plasters are coated over their whole area with a resin-rubber adhesive composition which comprises the active substance.

However, plasters of this kind, which usually have to be applied over a relatively large area, in some cases exhibit mechanical skin irritations after removal in the case of sensitive patients. After a prolonged period of application, their removal is to some extent painful.

A further disadvantage of the known thermally active plasters with an adhesive composition based on natural rubber which is applied in the form of a solution with organic solvents to the plaster backing is the comparatively low rate of release of the active substance.

The abovementioned disadvantages, and further disadvantages, apply also to active substance plasters comprising substances other than those mentioned.

For example, WO 94/02123 describes an active substance plaster based on pressure-sensitive hot-melt adhesive compositions and comprising low-melting and/or readily volatile active substances in a concentration of from 2.5 to 25% by weight.

Tapes or wound dressings can be fixed to joints or to the thigh only unsatisfactorily due to the mechanical stress. A frequent change of dressing is also customary in order to provide suitable active substances to the area to be treated on or around the joint.

In order to master the problem, plasters with substantial adhesion, shorts or stocking-like bandages are provided.

The object of the present invention is therefore also to provide an improvement in application for the care of the skin with skin patches. In particular it is an object of the present invention to provide a cellulite treatment set that is simple to use, also applicable for individual circumstances, sizes, areas of skin, and has no disadvantages regarding conventional cellulite treatments.

These objects are attained through a skin patch according to claim 1. Preferred embodiments of the patch are disclosed in the subordinate claims. Moreover, the invention also covers the use thereof. Furthermore, the objects are attained through a care set, comprising a skin patch and a wrapping.

It was surprising, and extremely astonishing to one skilled in the art, that a skin patch comprising a matrix adhering to human skin,
at least one cosmetic active substance, whereby the active substance is contained in the matrix,
attains the stated object.

SUMMARY OF THE INVENTION

The present invention provides a skin patch which comprises a matrix which adheres to human skin and at least one active cosmetic substance within the matrix.

In one aspect of the skin patch, the matrix may comprise at least one polymer which forms a gel in water, for example, acrylic acid and/or a salt thereof.

In another aspect, the matrix may comprise one or more polymers selected from polyisobutylene, styrene/isoprene/styrene-triblock copolymers, styrene/butadiene/styrene-triblock copolymers, styrene/butadiene rubber, synthetic polyisoprene, natural polyisoprene, polyamide, polyester, co-polyester, and polyurethane. For example, the matrix may comprise polyisobutylene.

In yet another aspect, the at least one active cosmetic substance may comprise one or more of carnitine, caffeine, capsaicin and derivatives thereof. For example, the at least one active cosmetic substance may comprise carnitine and/or a derivative thereof and may further comprise caffeine and/or a derivative thereof and/or may further comprise capsaicin and/or a derivative thereof. Further, the weight ratio of carnitine and/or a derivative thereof and caffeine and/or a derivative thereof may be from 100:1 to 1:1, and the weight ratio of carnitine and/or a derivative thereof and capsaicin and/or a derivative thereof may be from 100:1 to 1:1.

In yet another aspect, the skin patch may comprise from 0.01% to 10% by weight, e.g., from 0.1% to 1% by weight of carnitine and/or a derivative thereof, based on the total weight of the matrix.

In still further aspect, the skin patch may comprise at least one further active cosmetic substance. Non-limiting examples thereof include one or more of creatine, creatinine, alpha-glucosylrutin, taurine, serinol, isoserinol, Licorice Aqua PU, Licorice PU, silymarin, silyphos, lipoic acid, lipoic amide, green tea extract, white tea extract, vitamin C, 8-hexadecene-1,16-dicarboxylic acid, isoflavone, isoflavone-containing plant extract, soya extract, clover extract, ubiquinone Q10, sericoside, tyrosine sulfate, jojoba oil and aloe vera. For example, the at least one further active cosmetic substance may comprise green tea extract and/or it may comprise white tea extract.

In another aspect, the skin patch of the present invention may comprise at least 0.02% by weight and/or up to 15% by weight, e.g., up to 2% by weight, of one or more active cosmetic substances, based on the total weight of the matrix.

In another aspect, the skin patch of the present invention may comprise sodium polyacrylate/polyacrylic acid, carnitine, water, sodium carboxymethylcellulose, dihydroxyaluminum aminoacetate, hydroxypropylcellulose, glycerol, disodium edetate, kaolin, methyl para-hydroxybenzoate, propylene glycol and castor oil.

In yet another aspect, the matrix may exhibit an adhesion time value of higher than 5.

In a still further aspect, the skin patch may comprise a pad or a bandage and/or may have dimensions of from 8 cm×15 cm to 10 cm×20 cm.

The present invention also provides a kit which comprises the skin patch of the present invention as set forth above, including the various aspects thereof, and a gas and vapor permeable skin wrapping.

In one aspect of the kit, the skin wrapping may comprise a cuff. For example, the cuff may be capable of closing on itself at one end thereof and/or may have a conical shape and/or may be capable of exerting a pressure on skin, which pressure may be up to 10 mm Hg, e.g., from 4 mm Hg to 7 mm Hg.

The present invention further provided a skin patch which comprises a matrix which adheres to human skin and at least one active cosmetic substance within the matrix, said at least one active cosmetic substance comprising from 0.1% to 1% by weight of at least one of carnitine and a derivative thereof, based on a total weight of the matrix, and said matrix comprising a polymer of at least one of acrylic acid and a salt thereof.

In one aspect, the skin patch may exhibit an adhesion time value of higher than 5.

In another aspect, the skin patch may further comprise caffeine and/or a derivative thereof and/or it may further comprise capsaicin and/or a derivative thereof.

The present invention further provides a method of reducing cellulite. The method comprises applying to skin affected by cellulite the skin patch of the present invention as set forth above, including the various aspects thereof, or the kit of the present invention as set forth above, including the various aspects thereof.

The present invention further provides a method of reducing striae. The method comprises applying to skin affected by striae the skin patch of the present invention as set forth above, including the various aspects thereof, or the kit of the present invention as set forth above, including the various aspects thereof.

DETAILED DESCRIPTION OF THE INVENTION

The skin patch according to the invention encompasses all cosmetically applicable patches, such as patch, pad, wipes, plaster, dressings, cataplasm, bandages, masks.

According to the invention, a cosmetic, not a medicinally effective active substance, is contained in the adhesive matrix.

Polymers, polyisobutylenes or cataplasms which gel in water are preferred as the self-adhesive matrix. An adhesive mass based on polyacrylic acid or polyacrylates is particularly preferred.

The proportion of polymer which gels in water, such as, e.g., polyacrylic acid gel in the matrix regulates the adhesion. In particular the matrices disclosed in DE 10260873 and DE 10056010 are herewith an integral part of the present invention.

Polyacrylates that are advantageous according to the invention are acrylate-alkyl acrylate copolymers, in particular those from the group of carbomers or carbopols (Carbopol® is actually a registered trademark of B. F. Goodrich Company). In particular, the acrylate-alkyl acrylate copolymers which are advantageous according to the invention are characterized by the following structure:

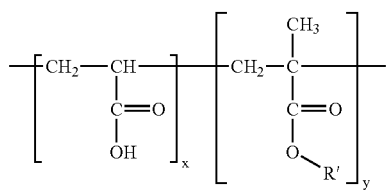

where R' is an alkyl radical, in particular a long-chain alkyl radical, and x and y represent numbers which symbolize the respective stoichiometric proportion of each of the comonomers.

According to the invention, particular preference is given to acrylate copolymers and/or acrylate-alkyl acrylate copolymers which are available under the trade names Carbopol® 1382, Carbopol® 981 and Carbopol® 5984 from B. F. Goodrich Company, preferably polyacrylates from the group of Carbopol grades 980, 981, 1382, 2984, 5984 and particularly preferably Carbomer 2001.

Also advantageous are copolymers of $C_{10-30}$-alkyl acrylates and one or more monomers of acrylic acid, of methacrylic acid or esters thereof which are crosslinked with an allyl ether of sucrose or an allyl ether of pentaerythritol.

The polymer which forms a gel in water, especially polyacrylic acid and/or copolymers thereof, is used preferably in an amount of 2-55% by weight, or preferably between 5-30% by weight.

The polymer matrices are produced without the use of organic solvents, preferably at 40-95° C., in standard commercial mixers/compounders or, continuously, in suitable extruders.

A further suitable polymer which forms a gel in water is, inter alia, baobab flour.

For example, the combination of polymer which gels in water (polyacrylic acid), sea algae extract, such as alginates and/or agar agar, and monohydric or polyhydric alcohol has proven to be advantageous. In this manner, using water, polymer which gels in water, sea algae extract and monohydric or polyhydric alcohol as starting materials, soft, smooth, self-adhesive hydrogel matrices can be produced in a targeted fashion as a basis for production and use as plasters, TTS, cataplasms or cosmetic pad/matrices.

In order to produce particular performance properties it is possible for the polymer matrices to be admixed with appropriate plasticizers, solubilizers, penetration enhancers, neutralizing agents such as, e.g., tromethamol (2-amino-2-(hydroxymethyl)-1,3-propanediol), triethanolamine (2,2',2"-nitrilotriethanol) or NaOH, fillers and/or other known additives, although it is not mandatory to add them.

In one embodiment which is particularly preferred in accordance with the invention, the polymer matrix or gel matrix contains active dermatological or active cosmetic substances for controlled local and/or systemic delivery onto/into the skin, in amounts of in total up to 35% by weight, preferably up to 15% by weight, in particular up to 2% by weight.

Since the matrix according to the invention is optionally also an application form which contains water, a cooling effect is obtained in addition, this effect already per se being cosmetically pleasant and contributing to well-being.

This positive effect can be intensified by the addition of further care constituents. Besides glycerin it is possible in particular to add serinol (3-amino-1,2-propanediol) and/or isoserinol (2-amino-1,3-propanediol) and also urea and PCA (pyrrolidone-carboxylic acid) as moisturizers. It is of course also possible to add further substances for this purpose.

Polyisobutylene PIB is also preferably used as a matrix system according to the invention.

In addition to PIB polyisobutylene, hydrophobic base polymers such as SIS (styrene/isoprene/styrene)-triblock copolymers, SBS (styrene/butadiene/styrene)-triblock copolymers, SBR (copolymers of styrene and butadiene), synthetic and/or natural polyisoprenes, polyamide, polyester, co-polyester, polyurethane and/or mixtures thereof are also possible as further matrices. From the multiplicity of known polymer matrices, polyacrylates and polyisobutylenes are particularly preferred.

Polyisobutylenes as the matrix base fulfill the requirements of a self-adhesive, gentle and painlessly detachable polymer matrix with particular effectiveness, and so it is logical to select the polyisobutylenes with preference as a matrix base.

SBR is a generic term for copolymers of styrene and butadiene, which contain both monomers usually in a weight ratio of approx. 23.5:76.5, in exceptional cases also 40:60, and the macromolecules of which predominantly have the structural units I and II:

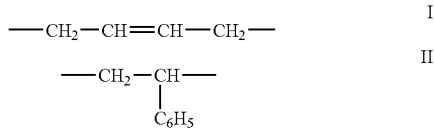

Water containing matrices according to the invention can be used in order to provide very dry areas of skin with moisture.

The polymer matrix according to the invention is thus extremely well suited as plaster, pad or skin patch for skin care and in particular for simple cooling purposes and, in addition equipped to be self-adhesive, easy to use.

It is also advantageous for the polymer matrix to be free of solvents to accordingly avoid the disadvantages of the prior art.

A preferred active cosmetic substance is carnitine, 3-hydroxy-4-(trimethylammmonium)-butyric acid betaine, with the structure

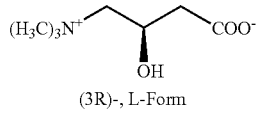

(3R)-, L-Form

The L form of carnitine is widespread in animal tissue, and a characteristic component of striated muscle primarily in dark types of meat. In vegetable foodstuffs, such as fruit, vegetables and grains, L-carnitine is present in only small amounts (<4 mg/100 g).

The total amount of L-carnitine in the human body is approx. 20-25 g. 98% of the reserves are stored in the cardiac musculature and skeletal muscles.

L-Carnitine serves as a carrier molecule in the transport of long-chain fatty acids through the mitochondrial membrane into the mitochondrial matrix chamber, while medium-chain and short-chain fatty acids can pass through it even without esterification with L-carnitine.

L-Carnitine is offered in numerous products as a food supplement. The target groups are (endurance) athletes and overweight people, to whom L carnitine is offered to improve performance or as a slimming aid ("fat burner"). The effectiveness is very controversial in both cases. Since a lack of L carnitine is very rare among healthy people, no advantage can be anticipated from a carnitine supplement. Carnitine is not exhausted in its biochemical function as a carrier, so that an increase in conversion in the area of lipometabolism does not lead to an increased need for carnitine. Conversely, an increased absorption of carnitine does not lead to an increase of fatty acid oxidation. An excess of carnitine is eliminated via the kidneys.

In the case of cardiovascular disease, through an increase in the β-oxidation of the fatty acids, increased ATP levels, a reduction in the blood count and tissue fat count (free fatty acids) and through an increase in the supply of blood to the heart, L-carnitine can improve the cardiac output and overall increase the heart's resistance to stress. In addition, a certain immunostimulation function is ascribed to L-carnitine, which is attributed to an increase in the activity of the granulocytes, T lymphocytes and killer cells.

However, it has surprisingly been proven that a self-adhesive matrix containing carnitine has a positive effect on the reduction of cellulite. The lymphocirculation is stimulated.

A skin patch according to the invention preferably containing carnitine is therefore suitable for the care of areas of the skin affected by cellulite.

Likewise a skin patch comprising a combination of an adhesive matrix of polyacrylic acid polymer and the active cosmetic substance carnitine has proven to be an advantageous treatment method of the areas of the skin affected by striae.

It is therefore preferred according to the invention to use the skin patch comprising polyacrylic acid polymers and carnitine contained therein for the cosmetic treatment of the areas of the skin affected by striae.

Carnitine or derivatives thereof are used in a proportion of from 0.01 to 10% by weight, preferably from 0.1 to 1% by weight, in particular 0.5% by weight, based on the total mass of the matrix.

Caffeine is preferably to be selected as a further active cosmetic substance according to the present invention.

Caffeine or also theine, guaranine, 1,3,7-trimethylxanthine, methyltheobromine, having the structure

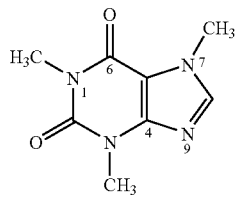

is found bound to chlorogenic acid in coffee beans (0.8-2.5%), in dried black tea (up to 5%; this tea caffeine also used to be called theine).

Caffeine has a lipolytic effect on the fatty tissue (increase in the free fatty acids). Furthermore the diuretic effect of coffee is also known.

Another preferred active substance within the scope of the present invention is capsaicin, (E)-N-(4-hydroxy-3-methoxybenzyl)-8-methyl-6-nonenamide; FEMA 3404, having the structure

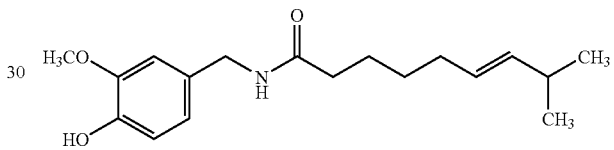

Capsaicin as a natural raw material is not usually understood to be the pure substance, but a mixture of capsaicin homologs with similar physiological effect, the so-called capsaicinoids. Thus the monograph of USP 28 describes capsaicin with a content of at least 55% capsaicin, the total contents of capsaicin and dihydrocapsaicin of at least 75% and the total contents of all other capsaicinoids, such as, e.g., nordihydrocapsaicin, as no more than 15%.

The term capsaicin thus can cover all the following homologs in different composition:

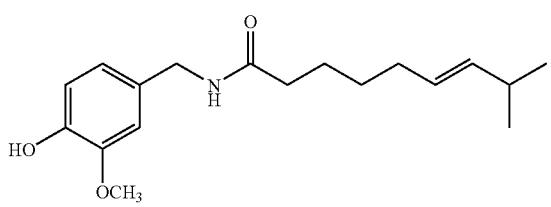

Capsaicin

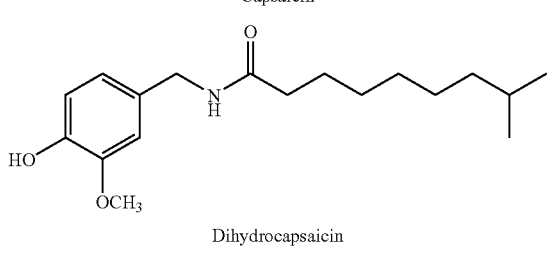

Dihydrocapsaicin

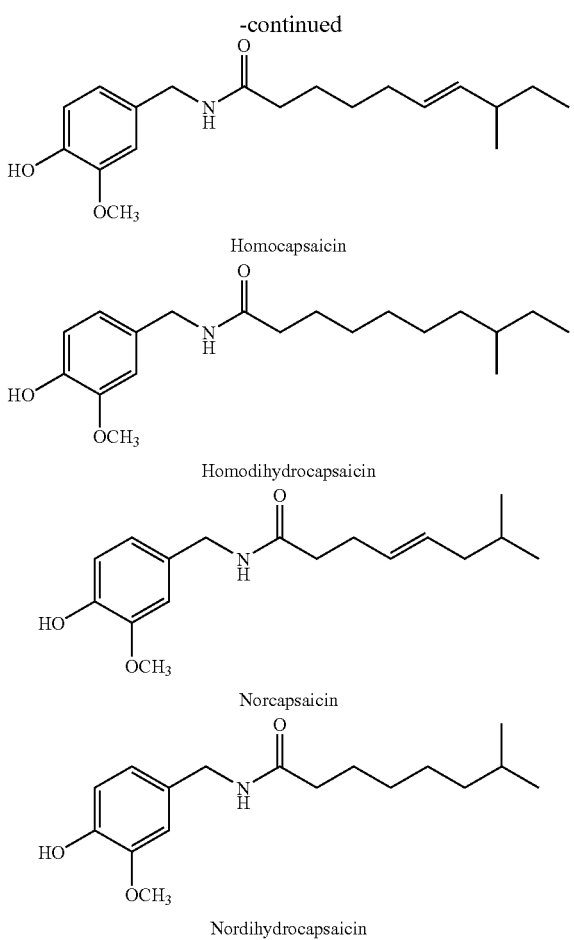

Homocapsaicin

Homodihydrocapsaicin

Norcapsaicin

Nordihydrocapsaicin

According to the invention the capsaicinoids can be incorporated as a powdery substance mixture as well as in the form of extracts containing capsaicin of different concentrations. For example, such extracts can be termed capsicum oleoresin or extractum capsici (fluidum) but are not limited thereto.

Likewise according to the invention, the capsaicinoids can be used in the form of triturations or pulverizations of the fruit components of the original hot pepper plants, e.g., as so-called chili powder.

Another homolog of the capsaicin according to the invention is nonanoic acid vanillylamide, also known as nonivamide for short.

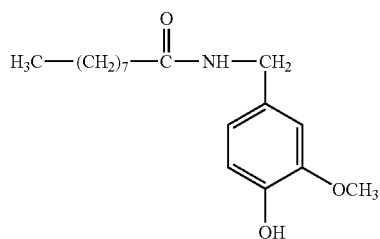

Nonivamide is produced synthetically and accordingly is called "synthetic capsaicin."

Even in small amounts, capsaicinoids on the mucous membranes cause tingling or a sensation of heat. For example, capsaicinoids are found in the known ABC plasters.

The term capsaicin used in the following encompasses all the natural and synethic capsaicinoids in all combinations and technical forms of application. In this regard, the mass ratios for capsaicin refer to the absolute amounts of the respective capsaicinoid/s in the matrix according to the invention, and not to the content or the amount of the form of the raw material containing capsaicin.

In contrast to the active substance cocktail known from the prior art, which in part are physiologically questionable, according to the invention only one (carnitine), two (carnitine—capsaicin, carnitin—caffeine) or three (carnitine—capsaicin—caffeine) are used.

Advantageously these active substances are integrated together into the self-adhesive matrix and are released therefrom onto the skin within the application time.

According to the invention the ratio of carnitine or derivatives thereof to capsaicin and/or caffeine is preferably 1 to 100 to 1, advantageously 1 to 1. That is, with a preferred proportion of carnitine of 0.5% by weight, a proportion of 0.5% by weight of caffeine has proven to be extremely effective.

The known heating effect of capsaicin, in combination with carnitine and its reduction effect of the tissue fats, leads to a reduction, already effective in low concentration, of the so-called orange-peel skin, cellulite.

Surprisingly, it has been shown that the combination of carnitine and capsaicin and/or caffeine leads to a synergy with respect to the care and treatment of deficient skin conditions, such as orange-peel skin or cellulite, Small varicose dilatations of the cutaneous veins, varicose veins or areas of the skin affected by striae.

The patchaccording to the invention which contains carnitine alone and/or in combination with capsaicin and/or caffeine in the matrix of the skin patch, shows an advantageous effect on the skin thus treated, the lymphatic circulation and the development of heat are stimulated.

This synergy is shown surprisingly positively in a skin patch that is in contact with the skin for several hours, up to eight hours.

In addition to carnitine, capsaicin and/or caffeine, other suitable active substances for the purposes of the invention can be added to the listed cosmetic matrices/pads either individually or in combination, in particular active substances that have a positive influence on the condition of the skin. Thus it has been shown that active substances for positively influencing aging skin which reduce the development of lines or else existing lines. Therefore, particularly preferred active substances are bioquinones, in particular ubiquinone Q10, creatine, creatinine, carnitine, acetyl carnitine, biotin, isoflavone and isoflavonoids, genistein, arctiin, cardiolipin, lipoic acid, antifreezing proteins, hop and hop-malt extracts, and or substances promoting the restructuring of the connective tissue, isoflavones and plant extracts containing isoflavones, such as, e.g., soya and clover extracts, which can also be used very readily in the matrices according to the invention. It is also found that the matrix is particularly suitable for using active substances for aiding the skin functions in dry skin (such as, for example, vitamin C, biotin, creatine, creatinine, propionic acid, glycerin, green tea extracts, white tea extracts or solutions, eucalyptus oil, urea and mineral salts, such as, for example, NaCl, sea minerals and osmolytes, such as, for example, taurine, inositol, betaine, quaternary ammonium compounds. In a similar way, the incorporation of active substances for alleviating or positively influencing irritative skin conditions, whether for sensitive skin in general or for skin irritated by noxae (UV light, chemicals) has proven to be advantageous. Mention is made here of active substances such as sericosides, various extracts of licorice, licochalcone A, silymarin and silyphos, dexpanthenol, ethanol, inhibitors of prostaglandin metabolism, in particular cyclooxygenase, and of leukotriene metabolism, in particular 5-lipoxygenase, but also the 5-lipoxygenase inhibitor protein, FLAP. The incorporation of pigmentation modulators has also proven to be advantageous. Mention is made here of active substances which reduce the pigmentation of the skin and thus lead to a cosmetically desired lightening of the skin and/or reduce the appearance of age spots and/or lighten existing age spots, such as tyrosine sulfate, dioic acid (8-hexadecene-1,16-dicarboxylic acid), lipoic acid and liponamide, various extracts of licorice, kojic acid, hydroquinone, arbutin, fruit acids, in particular alpha-hydroxy acids (AHAs), bearberry (Uvae ursi), ursolic acid, ascorbic acid, green tea extracts, aminoguanidine and/or pyridoxamine. In the same way, the matrices according to the invention proved to be an excellent basis for active substances that bring about an enhanced/more rapid tanning of the skin (Advanced Glycation Endproducts (AGE), lipofuscins, nucleic acid oligonucleotides, purines and pyrimidines, NO-releasing substances, be it with or without the influence of UV light.

The use of green tea extract is preferred, since in combination with carnitine the effect of caring for the skin and above all of reducing cellulite could be observed.

The secret of white tea is based on its careful preparation, so that it remains virtually unchanged. White tea extracts contain a high proportion of polyphenols, they are among the most highly effective antioxidants, which render free radicals harmless. The research concerned with these aspects of white tea is still relatively young. White teas are commercially available under the names Yin Zhen (silver needle) and Yin Long (silver dragon).

The use of white tea extract is therefore preferred since in combination with carnitine the effect of caring for the skin and above all of reducing cellulite could be observed.

Including carnitine, capsaicin and/or caffeine, the matrix contains a total of active substances of up to 35% by weight, preferably up to 15% by weight, very particularly preferably 0.02-2% by weight, based on the total mass of the matrix.

For the prophylaxis of oxidative and degenerative damage and in particular for the treatment of such damage it has surprisingly been found advantageous to add antioxidants to the cosmetic matrices/pads. The antioxidants are advantageously selected from the group consisting of amino acids, e.g., glycine, lysine, arginine, cysteine, histidine, tyrosine, tryptophan, and derivatives thereof (as salt, ester, ether, sugar, nucleotide, nucleoside, peptide and/or lipid compound), imidazoles, e.g., urocanic acid, and derivatives thereof as salt, ester, ether, sugar, nucleotide, nucleoside, peptide and/or lipid compound, peptides such as D,L-carnosine, D-carnosine, L-carnosine, anserine and derivatives thereof, e.g., as salt, ester, ether, sugar, thiol, nucleotide, nucleoside, peptide and/or lipid compound, carotenoids, carotenes, e.g., α-carotene, β-carotene, Ψ-lycopene, phytoene, and derivatives thereof, e.g., as salt, ester, ether, sugar, nucleotide, nucleoside, peptide and/or lipid compound, chlorogenic acid and derivatives thereof, as salt, ester, ether, sugar, thiol, nucleotide, nucleoside, peptide and/or lipid compound, aurothioglucose, propylthiouracil and other thiols, e.g., thioredoxin, lipoic acid, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters, and also salts thereof, dilauryl thiodipropionate, distearyl thiodipropionate, thiodipropionic acid and derivatives thereof, as salt, ester, ether, sugar, thiol, nucleotide, nucleoside, peptide and/or lipid compound, and also sulfoximine compounds, e.g. homocysteine sulfoximine, buthionine sulfones, penta-, hexa-, heptathionine sulfoximine, in very low tolerated doses, e.g., pmol to µmol/kg. Additionally (metal) chelating agents, e.g., apoferritin, desferral, lactoferrin, α-hydroxy fatty acids, palmitic acid, phytic acid, and derivatives thereof, as salt, ester, ether, sugar, thiol, nucleotide, nucleoside, peptide and/or lipid compound, a-hydroxy acids, e.g., citric acid, lactic acid, malic acid, humic acid, bile acid, bile extracts, bilirubin, biliverdin, melanin, EDTA, EGTA and derivatives thereof, unsaturated fatty acids and their derivatives, e.g., γ-linolenic acid, linoleic acid, oleic acid, folic acid and derivatives thereof, furfurylidenesorbitol and its derivatives, ubiquinone, ubiquinol, plastoquinone and derivatives thereof, as salt, ester, ether, sugar, thiol, nucleotide, nucleoside, peptide and lipid compound, vitamin C and derivatives, e.g., ascorbyl palmitate, Mg-ascorbyl phosphate, ascorbyl acetate, tocopherols and derivatives, e.g. vitamin E acetate, Trolox®, and also phenolic compounds and plant extracts comprising them, such as flavonoids, for example, e.g., glycosylrutin, ferulic acid, caffeic acid, furfurylideneglucitol, butylated hydroxytoluene, butylated hydroxyanisole, nordihydroguaiacic acid, nordihydroguaiaretic acid, trihydroxybutyrophenone and derivatives thereof, as salt, ester, ether, sugar, nucleotide, nucleoside, peptide and lipid compound, uric acid and derivatives thereof, mannose and derivatives thereof, as salt, ester, ether, sugar, thiol, nucleotide, nucleoside, peptide and lipid compound, zinc and its derivatives, e.g., ZnO, $ZnSO_4$, selenium and its derivatives, e.g., selenium methionine, ebselen, stilbenes and derivatives thereof, e.g., stilbene oxide, trans-stilbene oxide, and the derivatives that are suitable in accordance with the invention, as salt, ester, ether, sugar, thiol, nucleotide, nucleoside, peptide and/or lipid compound, of these stated active substances.

The matrix will contain the antioxidant or antioxidants in amounts of 0-35% by weight, preferably 0-15% by weight, very preferably 0.02%-2%.

Further examples of active substances which can be used include essential oils. By essential oils are meant plant-derived concentrates which as natural raw materials are used primarily in the fragrance and foodstuffs industries and are composed more or less of volatile compounds. Examples that may be mentioned of these compounds include 1,8-cineol, limonene, menthol, borneol and camphor. The term "essential oils" is often used for the volatile constituents still present in the plants. In their true sense, however, essential oils are understood to be mixtures of volatile compounds prepared by steam distillation from plant raw materials.

Essential oils are composed exclusively of volatile components, whose boiling points are in general between 150 and 300° C. They include predominantly hydrocarbons or monofunctional compounds such as aldehydes, alcohols, esters, ethers and ketones. Parent compounds are mono- and sesquiterpenes, phenylpropane derivatives and longer-chain aliphatic compounds.

In some essential oils, one constituent is dominant, for example, eugenol in clove oil, at more than 85%, while other essential oils constitute complex mixtures of the individual constituents. Often the organoleptic properties are determined not by the main components but by subsidiary or trace constituents, such as, for example, by the 1,3,5-undecatrienes and pyrazines in galbanum oil. The number of identified components in many of the commercially significant essential oils is up into the hundreds. Very many constituents are chiral, with very often one enantiomer being predominant or being present exclusively, such as (−)-menthol in peppermint oil or (−)-linalyl acetate in lavender oil, for example.

Preferred essential oils that may be mentioned include oleum eucalypti, oleum menthae piperitae, oleum camphoratum, oleum rosmarini, oleum thymi, oleum pini sibricum and oleum pini silvestris, and the terpenes 1,8-cineol and levomethanol.

Further essential oils that may be mentioned include oleum abietis albae, oleum anisi, oleum aurantii floris, oleum bergamottae, oleum calendulae infusum, oleum camphoratum, oleum caryophylli, oleum chamomillae, oleum cinnamomi ceylanici, oleum citri, oleum citronellae, oleum cupressi, oleum cymbopogonis, oleum jecoris, oleum lavendulae, oleum macidis, oleum majoranae, oleum melaleucae viridiflorae, oleum melissae, oleum menthae arvensis, oleum menthae piperatae, oleum millefolium, oleum myrrhae, oleum myrte, oleum oregani, oleum pini sibricum, oleum pinisilvestris, oleum salviae, oleum santali, oleum terebinthinae rectificat., oleum thymi, oleum valerianae, oleum zingiberis and/or tea tree oil.

Peppermint oils are essential oils obtained by steam distillation from leaves and blossoms of various varieties of peppermint, and occasionally also those from Mentha arvensis.

Citrus oils are essential oils obtained from the peel of citrus fruits (bergamot, grapefruit, lime, mandarin, orange, lemon), often also called agrumen oils.

Citrus oils are composed largely of monoterpene hydrocarbons, principally limonene (exception: bergamot oil, which contains only about 40%).

Menthol can be used for example for surface anesthesia in cases of skin irritation as a result of light burns. The products used in this way generate a pleasant feeling of cold and can be used for cooling skin irritations, e.g., mild sunburn and shaving burn that do not require specialist medical treatment.

Menthol has three asymmetric C atoms and accordingly exists in four diastereomeric pairs of enantiomers (cf. the formulae; the other four enantiomers are the corresponding mirror images).

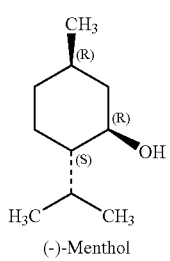

(-)-Menthol (1)

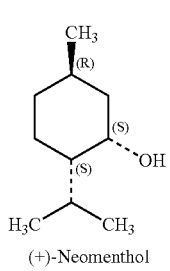

(+)-Neomenthol (2)

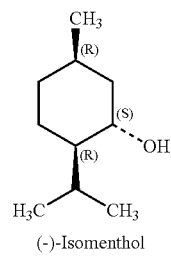

(-)-Isomenthol (3)

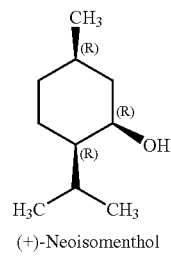

(+)-Neoisomenthol (4)

The diastereoisomers, which can be separated by distillation, are referred to as neoisomenthol, isomenthol, neomenthol [(+) form: a constituent of Japanese peppermint oil] and menthol. The most important isomer is (−)-menthol (levomenthol), shining prisms with a strong peppermint-like odor.

As further active substances it is possible to add camphor, for example, to the matrix in order to treat skin irritations/mild pain, neuralgias and inflammation. By camphor is meant 2-bornanone, 1,7,7-trimethylbicyclo[2.2.1]heptan-2-one; see diagram below.

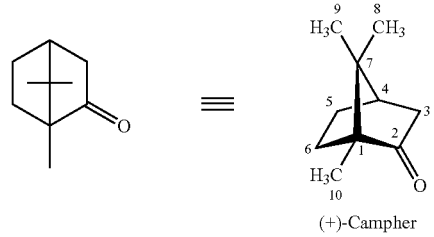

(+)-Campher

For advantageous embodiments of hydrogels/cataplasms of the invention it is also possible to mention in addition active hyperemic substances such as synthetic active substances such as nicotinic acid derivatives, preferably benzyl nicotinate or propyl nicotinate, and anti-inflammatories and/or analgesics.

By way of example mention may be made of nicotinic acid benzylester

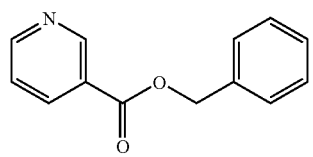

Benzyl nictotinate.

Flavone and its derivatives, often also collectively called "flavones," are also advantageous additives in the sense of the present invention. They are characterized by the following basic structure (substitution positions indicated):

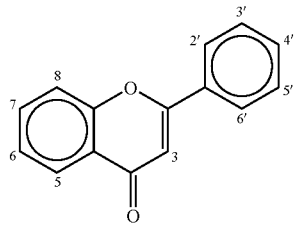

Some of the more important flavones, which can also be used with preference in preparations of the invention, are listed in the table below:

|  | OH substitution positions | | | | | | | |
|---|---|---|---|---|---|---|---|---|
|  | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | + | + | − | − | − | − | − |
| Galangin | + | + | + | − | − | − | − | − |
| Apigenin | − | + | + | − | − | − | + | − |
| Fisetin | + | − | + | − | − | + | + | − |
| Luteolin | − | + | + | − | − | + | + | − |
| Campherol | + | + | + | − | − | − | + | − |
| Quercetin | + | + | + | − | − | + | + | − |
| Morin | + | + | + | − | + | − | + | − |
| Robinetin | + | − | + | − | − | + | + | + |
| Gossypetin | + | + | + | + | − | + | + | − |
| Myricetin | + | + | + | − | − | + | + | + |

In nature, flavones occur ordinarily in glycosylated form.

In accordance with the invention the flavonoids are preferably chosen from substances of the generic structural formula

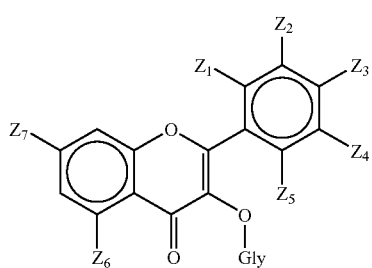

where $Z_1$ to $Z_7$ are chosen independently of one another from H, OH, alkoxy and also hydroxyalkoxy, where the alkoxy and hydroxyalkoxy groups respectively may be branched and unbranched and may have 1 to 18 C atoms, and where Gly is chosen from mono- and oligoglycoside residues.

In accordance with the invention the flavonoids can, however, also be chosen advantageously from substances of the generic structural formula

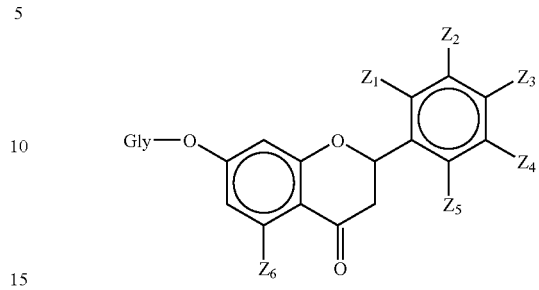

where $Z_1$ to $Z_6$ are chosen independently of one another from H, OH, alkoxy and also hydroxyalkoxy, where the alkoxy and hydroxyalkoxy groups respectively may be branched and unbranched and may have 1 to 18 C atoms, and where Gly is chosen from mono- and oligoglycoside residues.

Such structures can be chosen with preference from substances of the generic structural formula

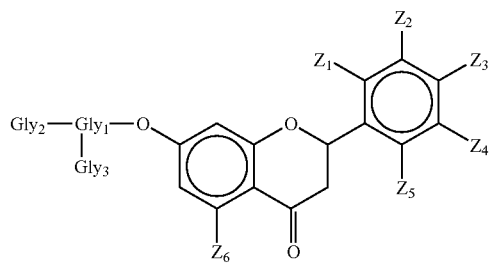

where $Gly_1$, $Gly_2$ and $Gly_3$ independently of one another represent monoglycoside residues or $Gly_2$ and $Gly_3$ may also, individually or together, represent saturations by hydrogen atoms.

Preferably $Gly_1$, $Gly_2$ and $Gly_3$ are chosen independently of one another from hexosyl radicals, particularly rhamnosyl radicals and glucosyl radicals. However, other hexosyl radicals can as well be used with advantage where appropriate, examples being allosyl, altrosyl, galactosyl, gulosyl, idosyl, mannosyl and talosyl. It may also be of advantage in accordance with the invention to use pentosyl radicals.

$Z_1$ to $Z_5$ advantageously are chosen independently of one another from H, OH, methoxy, ethoxy and also 2-hydroxyethoxy, and the flavone glycosides have the structure:

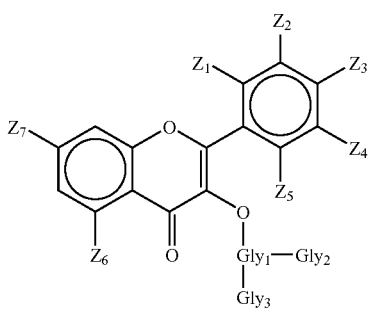

The flavone glycosides of the invention which become of particular advantage are those from the group represented by the following structure:

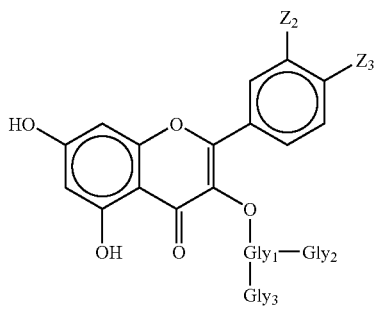

where $Gly_1$, $Gly_2$ and $Gly_3$ independently of one another represent monoglycoside residues or oligoglycoside residues. $Gly_2$ and $Gly_3$ may also, individually or together, represent saturations by hydrogen atoms.

Preferably $Gly_1$, $Gly_2$ and $Gly_3$ independently of one another are chosen from hexosyl radicals, in particular rhamnosyl radicals and glucosyl radicals. However, other hexosyl radicals can as well be used with advantage where appropriate, examples being allosyl, altrosyl, galactosyl, gulosyl, idosyl, mannosyl and talosyl. It may also be an advantage in accordance with the invention to use pentosyl radicals.

In the sense of the present invention it is particularly advantageous to choose the flavone glycoside or glycosides from α-glucosylrutin, α-glucosylmyricetin, α-glucosylisoquercitrin, α-glucosylisoquercetin and α-glucosylquercitrin.

Of particular preference in accordance with the invention is α-glucosylrutin.

Also advantageous in accordance with the invention are naringin (aurantiin, naringenin-7-rhamnoglucoside), hesperidin (3',5,7-trihydroxy-4'-methoxyflavanone-7-rutinoside, hesperidoside, hesperetin-7-O-rutinoside), rutin (3,3',4',5,7-pentahyd roxyflyvone-3-rutinoside, q uercetin-3-rutinoside, sophorin, birutan, rutabion, taurutin, phytomelin, melin), troxerutin (3,5-dihydroxy-3',4',7-tris(2-hydroxyethoxy) flavone-3-(6-(O-(6-deoxy-α-L-mannopyranosyl)-β-D-glu-copyranoside)), monoxerutin (3,3',4',5-tetrahyd roxy-7-(2-hydroxyethoxy)-flavone-3-(6-(O-(g -deoxy-α-L-mannopyranosyl)-β-D-gluco-pyranoside)), dihydrorobinetin (3,3',4',5',7-pentahydroxyflavanone), taxifolin (3,3',4',5,7-penta-hydroxyflavanone), eriodictyol-7-glucoside (3',4',5,7-tetrahyd roxyflavanone-7-glucoside), flavanomarein (3',4',7, 8-tetrahydroxyflavanone-7-glucoside) and isoquercetin (3,3', 4',5,7-pentahydroxyflavanone-3-(β-D-glucopyranoside)) or derivatives thereof.

According to the invention, the requirement for a self-adhesive skin patch is met surprisingly simply and effectively. The skin patch according to the invention comprising preferably carnitine as active substance and polyacrylic acid as the basis of the adhesive matrix, on the one hand has a good adhesion to the skin, which must be maintained over the entire period of the intended dosage of the active substance, and on the other hand a removability that is pain-free and does not leave any residue.

Since adhesion and consistency of an adhesive matrix containing the active substance result from the interaction of the individual components, actually the production of a skin patch is associated with many problems, as shown in the prior art.

However, these problems surprisingly have been solved by the particularly preferred variant. A skin patch according to the invention has proven to be preferred in which a combination of preferred polyacrylate adhesive mass (sodium polyacrylate/polyacrylic acid sol. 20%), carnitine as active cosmetic substance and the following constituents of the patch are selected:

Water, sodium carboxymethylcellulose, dihydroxyaluminum aminoacetate, hydroxypropylcellulose, glycerol, disodium edetate, kaolin, methyl parahydroxybenzoate, propylene glycol and/or ricinus communis (castor oil).

The skin patches preferred according to the invention and thus produced can be easily placed onto the skin and due to the special adhesive force, exert a pressure on the skin which reduces the appearance of cellulite or striae.

The essential influencing variable on exerting pressure is the material of the plaster and its consistency. If it is, e.g., a relatively flexible, elastic material, the material can avoid the pressure generated on being applied to the skin. Thus no pressure is exerted on the skin. However, if the material is rigid and inflexible, this is not compatible with the patient's comfort when worn for a long time.

Further influencing variables on the pressure exerted, which also indirectly concern the plaster material properties, are:
stretchability of the material upon application, i.e., when the plaster is greatly stretched over the skin and corresponding adhesion to the skin, the skin could be contracted and the pressure is directed in a counter-productive manner
moisture of the skin and thus also moisture-permeability of the material
adhesion to the skin
dynamic pressures and/or shear forces by motion of the area of the skin.

According to the invention, these influencing variables are optimally coordinated with one another through the preferably selected constituents of the adhesive matrix, the carrier material and the active cosmetic substances.

It has proven to be advantageous according to the invention for the reduction of the skin phenomena affected by cellulite if the skin patch has an adhesion time value of greater than 5 s. The adhesion time value is determined according to a standard measurement method, as outlined briefly below.

A measurement of the adhesion time value is carried out on a test instrument according to FIG. 1.

FIG. 1 shows an inclined plane with a pitch of 30° on which the skin patch to be tested is placed with the adhesive side (3) uppermost. The upper and lower part is covered by cardboard (2) so that a stretch of 5 cm remains. The steel ball (1) is placed at the head of the inclined plane.

Before each measurement, steel balls (diameter 19.0 mm, mass 28.2 g) are cleaned of all greasy residue and other contaminants first in toluene and then in anhydrous acetone. The flash time of the solvent up to the use of the steel balls must be at least 2 minutes and may be no longer than 10 minutes.

The self-adhesive skin patch to be tested is placed with the carrier side down in the middle of an inclined plane (30°) so that the patch ends overlap the markings made at the side on the inclined plane. Then the upper part of the inclined plane, starting from the upper edge, is covered by means of a sheet of paper (standard copier paper or comparable quality), for a length of 10 cm, the paper is, if necessary, folded over the edge and secured from slipping by a steel pin.

Below the covered portion of the inclined plane, the measuring length follows the skin patch with the adhesive mass layer revealed. The length of the respective measuring length is 5 cm. Subsequently, the lower part of the plane, starting from the lower edge of the respective measuring length, is likewise covered with paper. Then a steel ball is placed by hand (wear powder-free gloves) on the upper end of the inclined plane and allowed to roll with the slightest possible application of force. As soon as the steel ball comes to a stop on the skin patch, a stop watch is started (see FIG. 1).

The steel ball must be held by the adhesive layer of the patch within the revealed section of the skin patch for at least 5 seconds in order to meet the requirement of the adhesion time value, i.e., it must reach an adhesion time value of greater than 5.

These tests have shown that the skin patches according to the invention comprising the following constituents show a corresponding adhesion time value. The matrix according to the invention and adhering to the human skin and containing carnitine as the active cosmetic substance, has an adhesion time value of greater than 5 and thus has the necessary characteristic in order to meet the requirements for the adhesive force over the duration of application (of up to 8 h), a pain-free removal leaving no residue and an adhesion with no irritation of the skin.

A polyacrylate adhesive mass containing carnitine and the special constituents* with an adhesion time value >5 is preferred.

TABLE adhesion time value

| Adhesive mass | Active substance | Adhesion time value [s] |
|---|---|---|
| Polyacrylates* | Carnitine | >5 |
| Polyacrylates* | Carnitine, capsaicin | >5 |
| Polyacrylates* | Carnitine, caffeine (1:1) | >5 |

*Polyacrylates containing: sodium polyacrylate/polyacrylic acid sol. 20%, water, sodium carboxymethylcellulose, dihydroxyaluminum, aminoacetate, hydroxypropylcellulose, glycerol, disodium edetate, kaolin, methyl parahydroxybenzoate, propylene glycol and ricinus communis (castor oil).

For use as a patch, plaster or cosmetic matrix/cosmetic pad, the gel matrices of the invention are pressed, rolled or the like as a layer onto a release medium made of paper, film or the like and are laminated on the reverse with any desired backing material such as, for example, a polymer film, textiles or the like. With particular preference in accordance with the invention the gel matrices are applied in the hot state by a metering pump to a backing material, and with very particular preference are configured in a three-dimensional form by means of corresponding cavities in the presses or roller mechanisms. The shape of the plaster or cosmetic matrix produced is determined by the shape of the cavities and is not subject to any restriction; it may, for example, be ellipsoidal with edges which flatten off, or may, for example, be angular in configuration.

With particular advantage the gel matrix of the invention is applied on a flexible cover layer, particularly when used as a skin patch, plaster or cosmetic matrix. A corresponding plaster or a corresponding cosmetic matrix is constructed from a backing such as films, nonwovens, wovens, foams, etc., the adhesive matrix, and liner film, liner paper or release paper in order to protect the adhesive matrix prior to the use of the plaster.

In a further preferred embodiment of the invention, backings used are polymer films, nonwovens, wovens and combinations thereof. Backing materials available for selection include polymers such as polyethylene, polypropylene, polyesters, polyethers, polyether-ester copolymers and polyurethane or else natural fibers.

In summary it can be stated that suitable backing materials encompass all rigid and elastic sheet-like structures of synthetic and natural raw materials. Preference is given to backing materials which can be employed such that they fulfill properties of a functional dressing. Listed by way of example are textiles such as wovens, knits, lays, nonwovens, laminates, nets, films, foams and papers. In addition it is also possible for these materials to be pretreated and/or after-treated. Customary pretreatments are corona and hydrophobization; common after-treatments are calendering, heat-treating, laminating, punching and enveloping.

It is particularly advantageous if the backing material is sterilizable, preferably γ(gamma)-sterilizable.

These backing materials in accordance with the invention can be, e.g., provided point-wise with strongly adhesive polymers such as polyisobutylene, SEBS block polymers, natural rubbers and/or synthetic rubbers, polyurethane or the like by screen printing or analogous methods, which outwardly overlap the applied hydrogel matrix at the side edges. Matrices of the invention manufactured in this form can be affixed self-adhesively to parts of the body that are under severe mechanical stress, such as elbows or knee joints, where the inherent adhesion of the hydrogels/cataplasms is no longer sufficient for durable application.

Finally the matrix can be enveloped or provided with an anti-adhesive backing material, such as siliconized paper. On its self-adhesive side which later faces the skin, the cosmetic matrix of the invention is lined over its whole width, until used, usually with an anti-adhesive backing material. This protects the self-adhesive layer from the gel matrix's adhesive, which possesses good skin compatibility and which has preferably been applied by a transfer method, and additionally stabilizes the product as a whole. The lining can be designed, in a known way, in once piece or, preferably, in two parts.

Further embodiments may be such that between the reverse of the matrix and the lining backing there is a second matrix possessing higher active-substance solubility, as a reservoir. Instead of a second matrix and backing, this might also be a thermoformed film with pure active substance.

Located on part (e.g., at the edge) of the adhesive side of the matrix is a second matrix possessing high bond strength for the purpose of additional fixing, but possessing insufficient active-substance solubility.

The active substance-free matrix is located between two non-anchoring films and is utilized for fixing.

The subject matter of the present invention is further the use of the cosmetic skin patch for skin care, in particular of those parts of the skin affected by cellulite or striae. In particular the use of the active-substance-doped gel matrices for use as PADs for the cosmetic and beneficial treatment of unwanted skin phenomena, such as cellulite or striae, is to be emphasized with preference.

The use of the polymer matrix as cosmetic or dermatological pads or plasters is suitable particularly in a flat embodiment with a total area of 0.2 to 1000 $cm^2$. With this, for example, large (up to 1000 $cm^2$) regions on the thighs are covered for the purpose of treating the orange-peel skin.

Preference is given to the use of the self-adhesive polymer matrix in two- or three-dimensional embodiment with a polymer matrix weight fraction of 0.1 to 1000 g, in particular of 14 g per patch. The shape in this case may be round, oval, angular or designed in accordance with the sections of the skin.

The invention further covers the combination of the skin patch with a wrapping compressing the skin up to a certain pressure.

It is known from tests that the lymphatic circulation of the skin can be stimulated by compression. However, if the compression is too strong, it can lead to blockages and as a result to edema or thrombosis.

The pressure values of the patches or set applied to human skin have been determined as another characteristic value of the skin patches or the set according to the invention.

The measurement was carried out in a single-axis tensile test in accordance with DIN 53835—ensile stress with repeated stress between constant yield strengths and immediate reverse at the reverse points. The upper yield strength was established at 30%. The determination of the tensile force relating to elongation of the patch under stress was made in the $5^{th}$ cycle for the elongation that corresponded to the elongation of the patch after application to the leg. The calculation of the pressure was made using Laplace's equation from tensile force, leg circumference and patch or wrapping width.

The pressures determined according to the invention were between approx. 4-7 mmHg.

Patches according to the invention which comprise such pressure values are therefore preferred.

A patch or a set is therefore preferred according to the invention which consists of skin patch and wrapping that generates a pressure of up to a maximum of 10 mm Hg on the skin.

The set is thereby designed as described at the outset, so that a maximum pressure of 10 mm Hg is generated on the skin.

A wrap is known from the prior art which is called "wrapping". A type of cellophane casing is thereby drawn over the areas of the skin affected by cellulite. A disadvantage is the completely occlusive covering of the skin, which can lead to skin macerations, itching and other unpleasant skin phenomena.

The invention was designed to avoid these disadvantages.

Bandages, tape, stockings, shorts and/or cuffs can be contemplated as wrapping as well as a combination thereof.

According to the invention a cuff is selected as a wrapping, which is elastic up to a certain degree and air-permeable and steam-permeable.

The cuff preferably has a conical section. Thus when applied to the thigh a disadvantageous greater compression on the upper section of the thigh towards the hip is avoided.

The cuff is equipped with one end being self-adhesive to itself so that it can be attached to itself.

The result of this is that there is no need to supply different cuffs for users with differing sizes and shapes. According to the invention, due to the elasticity and the properties of closing itself, the cuff thus covers all the standard sizes and a "one size fits all" situation is advantageously created for the manufacturer.

Advantageously markings are made on the cuff that make it easy for the user to generate sufficient pressure with the cuff, depending on the circumference of the thigh.

Numerous materials based on film, nonwoven, woven, gel or foam are already known as a backing material for the cuff and are also used in practice. The materials must be tolerated by the skin, permeable to air and steam as well as possible to mold well and soft. Due to these requirements, often a carrier that is as thin or soft as possible is preferred. For handling and in use, however, sufficient strength and if necessary a limited stretchability are also required of the backing material. Furthermore the backing material should also have sufficient strength and a limited stretchability even after being soaked.

Thin backings, in particular those of nonwovens, are readily permeable to air and steam.

Suitable backing materials encompass elastic sheet-like structures of synthetic and natural raw materials. Preference is given to backing materials which can be employed such that they fulfill properties of a functional dressing. Listed by way of example are textiles such as wovens, knits, lays, nonwovens, laminates, nets, films, foams and papers which have a stretchability of at least 10% at a stress of 10 N/cm. Moreover, combinations of the listed materials are also suitable.

In addition it is also possible for these materials to be pretreated and/or after-treated. Customary pretreatments are corona and hydrophobization; common after-treatments are calendering, heat-treating, laminating, punching and enveloping, UV/IR irradiation or electron irradiation.

The invention thus advantageously covers a combination of self-adhesive skin patch and cuff according to the invention. This combination is predestined as a set for skin care and in particular for the treatment of cellulite.

In application the set according to the invention can comprise a cuff and 4 to 10 patches so that a long-term and thus effective treatment is ensured.

In skin care, and in particular in the treatment of cellulite, the skin patch according to the invention, advantageously containing carnitine or carnitine and capsaicin, is applied to, e.g., the side portion of the thigh. Due to the self-adhesive property of the skin patch with an adhesion time value of >5, this is immediately fixed and does not slip. Subsequently the user can if necessary turn over the cuff and close it easily because of the end closing to itself, depending on the desired degree of pressure and the size of the thigh.

Due to the advantageous design of the skin patch with skin care ingredients, non-irritating adhesive matrix, pain-free detachability and cuff that is not irritating to the skin and is permeable to air and steam, the user will not experience any unpleasantness, even with longer application.

A preferred application time is up to 8 hours, so that according to the invention the skin patch can be preferably worn overnight.

What is claimed is:

1. A kit comprising a skin patch, wherein the skin patch comprises a matrix which is capable of adhering to human skin and comprises at least one polymer and one or more active cosmetic substances which comprise carnitine, and wherein the kit further comprises a gas and vapor permeable skin wrapping that comprises a cuff.

2. The kit of claim 1, wherein the at least one polymer gels in water.

3. The kit of claim 2, wherein the at least one polymer comprises a polymer of at least one of acrylic acid and a salt thereof.

4. The kit of claim 3, wherein the at least one polymer comprises a polymer of sodium acrylate and acrylic acid.

5. The kit of claim 1, wherein the at least one polymer comprises one or more of polyisobutylene, styrene/isoprene/styrene-triblock copolymers, styrene/butadiene/styrene-triblock copolymers, styrene/butadiene rubber, synthetic polyisoprene, natural polyisoprene, polyamide, polyester, co-polyester, and polyurethane.

6. The kit of claim 5, wherein the at least one polymer comprises polyisobutylene.

7. The kit of claim 1, wherein the skin patch comprises from 0.01% to 10% by weight of carnitine, based on a total weight of the matrix.

8. The kit of claim 7, wherein the skin patch comprises from 0.1% to 1% by weight of carnitine.

9. The kit of claim 1, wherein the skin patch comprises at least one further active cosmetic substance.

10. The kit of claim 9, wherein the at least one further active cosmetic substance comprises white tea extract.

11. The kit of claim 1, wherein the skin patch comprises up to 2% by weight of the one or more active cosmetic substances.

12. The kit of claim 1, wherein the skin patch further comprises at least one antioxidant.

13. The kit of claim 1, wherein the skin patch further comprises at least one essential oil.

14. The kit of claim 1, wherein the skin patch further comprises at least one moisturizer selected from glycerin, serinol, isoserinol, urea and pyrrolidone carboxylic acid.

15. The kit of claim 1, wherein the skin patch further comprises caffeine.

16. The kit of claim 1, wherein the skin patch further comprises capsaicin.

17. The kit of claim 3, wherein the matrix comprises from 2% to 55% by weight of the polymer of at least one of acrylic acid and a salt thereof.

18. The kit of claim 4, wherein the matrix comprises from 5% to 30% by weight of the polymer of sodium acrylate and acrylic acid.

19. The kit of claim 1, wherein the skin patch comprises a polymer of sodium acrylate and acrylic acid, carnitine, water, sodium carboxymethylcellulose, dihydroxyaluminum aminoacetate, hydroxypropylcellulose, glycerol, disodium edetate, kaolin, methyl para-hydroxybenzoate, propylene glycol and castor oil.

20. The kit of claim 1, wherein the matrix exhibits an adhesion time value of higher than 5.

21. A kit comprising a skin patch, wherein the skin patch comprises a matrix which is capable of adhering to human skin and comprises at least one polymer and one or more active cosmetic substances, the one or more active substances comprising from 0.1% to 1% by weight of carnitine, based on a total weight of the matrix, and the at least one polymer comprising a polymer of at least one of acrylic acid and a salt thereof, and wherein the kit further comprises a gas and vapor permeable skin wrapping that comprises a cuff.

22. The kit of claim 21, wherein the at least one polymer comprises a polymer of sodium acrylate and acrylic acid.

23. The kit of claim 22, wherein the matrix comprises from 5% to 30% by weight of the polymer of sodium acrylate and acrylic acid.

24. The kit of claim 22, wherein the patch exhibits an adhesion time value of higher than 5.

25. The kit of claim 22, wherein the matrix further comprises at least one antioxidant.

26. The kit of claim 22, wherein the matrix further comprises at least one essential oil.

27. The kit of claim 22, wherein the matrix further comprises at least one moisturizer selected from glycerin, serinol, isoserinol, urea and pyrrolidone carboxylic acid.

28. The kit of claim 22, wherein the matrix further comprises caffeine.

29. The kit of claim 22, wherein the matrix further comprises capsaicin.

30. The kit of claim 1, wherein the cuff is capable of closing on itself at one end thereof.

31. The kit of claim 1, wherein the cuff has a conical shape.

32. The kit of claim 1, wherein the skin wrapping is capable of exerting a pressure on skin, which pressure is up to 10 mm Hg.

33. The kit of claim 32, wherein the pressure is from 4 mm Hg to 7 mm Hg.

34. The kit of claim 1, wherein the kit comprises from 4 to 10 patches.

35. The kit of claim 21, wherein the cuff is capable of closing on itself at one end thereof.

36. The kit of claim 21, wherein the cuff has a conical shape.

37. The kit of claim 21, wherein the skin wrapping is capable of exerting a pressure on skin, which pressure is up to 10 mm Hg.

38. The kit of claim 37, wherein the pressure is from 4 mm Hg to 7 mm Hg.

39. The kit of claim 21, wherein the kit comprises from 4 to 10 patches.

* * * * *